United States Patent
Chen et al.

(10) Patent No.: US 9,518,304 B2
(45) Date of Patent: Dec. 13, 2016

(54) NICOTINE RESISTANT MICROORGANISMS

(71) Applicant: Tyton Biosciences, LLC, Danville, VA (US)

(72) Inventors: Hsi-Chuan Chen, Danville, VA (US); Peter Majeranowski, Danville, VA (US); Igor Kostenyuk, Danville, VA (US); Iulian Bobe, Danville, VA (US)

(73) Assignee: Tyton Biosciences, LLC, Danville, VA (US)

( * ) Notice: Subject to any disclaimer, the term of this patent is extended or adjusted under 35 U.S.C. 154(b) by 0 days.

(21) Appl. No.: 14/723,397

(22) Filed: May 27, 2015

(65) Prior Publication Data

US 2015/0344978 A1 Dec. 3, 2015

Related U.S. Application Data

(60) Provisional application No. 62/004,176, filed on May 28, 2014.

(51) Int. Cl.
*C12P 7/10* (2006.01)
*C12R 1/865* (2006.01)
*C12N 1/16* (2006.01)
*C12N 1/36* (2006.01)

(52) U.S. Cl.
CPC .............. *C12R 1/865* (2013.01); *C12N 1/16* (2013.01); *C12N 1/36* (2013.01); *C12P 7/10* (2013.01); *Y02E 50/16* (2013.01)

(58) Field of Classification Search
CPC .................................. C12P 7/10; Y02E 50/16
See application file for complete search history.

(56) References Cited

U.S. PATENT DOCUMENTS

2004/0064849 A1* 4/2004 Goossens ........... C12N 15/8242
800/278

* cited by examiner

*Primary Examiner* — Rosanne Kosson
(74) *Attorney, Agent, or Firm* — NK Patent Law, PLLC

(57) ABSTRACT

Compositions and methods are provided for enhanced production of ethanol from fermentation of tobacco biomass. Nicotine resistant microorganisms are provided, as well as methods for making these nicotine resistant microorganisms. A biologically pure culture is provided of a nicotine resistant *Saccharomyces cerevisiae* strain or a mutant thereof having all the identifying characteristics thereof. Methods are provided for producing ethanol from fermentation of tobacco biomass in which the nicotine resistant microorganisms are used in the fermentation of the tobacco biomass, wherein a higher amount of ethanol can be produced from the fermentation. The nicotine resistant yeast strains of the present disclosure can improve ethanol production in tobacco biomass extract fermentations and shorten the fermentation time.

14 Claims, 3 Drawing Sheets

NICOTINE RESISTANT MICROORGANISMS

CROSS REFERENCE TO RELATED APPLICATIONS

This application claims the benefit of U.S. provisional patent application No. 62/004,176 filed May 28, 2014, the disclosure of which is hereby incorporated by reference in its entirety.

TECHNICAL FIELD

The present disclosure relates to nicotine resistant microbial strains and methods for their preparation and use for fermentation of tobacco biomass.

BACKGROUND

Renewable energy from biomass has the potential to reduce dependency on fossil fuels and the corresponding negative environmental impact. Realization of this potential will require the development of high yielding biomass production systems. A major advantage for utilizing tobacco as an energy biomass feedstock is that it is a well established non-food industrial crop that is cultivated in more than 100 countries around the world. When grown for energy production rather than smoking, tobacco biomass can be generated more efficiently and inexpensively than almost any other agricultural crop. In addition, tobacco can be grown on land not involved in food production, such that its production for energy biomass is not replacing growth of a food crop. Further, use of tobacco as a renewable resource as energy biomass promotes energy independence.

As a biomass for cellulosic ethanol fermentation, tobacco has two main advantages over existing feedstocks: a high amount of easily fermentable sugars, and a low content of lignin, which in other lignocellulitic feedstock significantly hampers the fermentation process and contributes to high costs. Tobacco biomass is naturally rich in sugars and starch and low-lignin cellulose. While there is wide variation among tobacco types, generally tobacco contains 15-20% sugars, 8-14% starch and 30-40% cellulose per dry weight.

However, and in contrast to the kernel of corn plants, a major disadvantage to use of tobacco for ethanol fermentation is that the sugar in tobacco is not largely localized in a tissue that can be easily fermented to produce ethanol. An additional disadvantage is that tobacco biomass contains levels of nicotine that can be toxic to certain organisms such as the microbial strains used in the fermentation reaction.

Thus, an unmet need remains for improved compositions and methods for production of ethanol from fermentation of tobacco biomass. The present disclosure provides such improved compositions and methods.

SUMMARY OF THE INVENTION

In one embodiment, the presently disclosed subject matter provides a nicotine resistant microorganism produced according to a process comprising: (a) culturing a microorganism in a medium conducive to growth, wherein the medium comprises a first concentration of nicotine that retards but does not inhibit growth of the microorganism; (b) selecting a single colony of the microorganism and inoculating the single colony into a fresh culture of the medium conducive to growth, wherein the fresh medium comprises a second concentration of nicotine that is incrementally higher than the first concentration and that retards but does not inhibit growth of the microorganism; and (c) repeating step (b) until the desired concentration of nicotine is achieved or until growth of the microorganism is completely inhibited, such that the microorganism produced is resistant to the desired concentration of nicotine.

In one embodiment, the presently disclosed subject matter provides a method for generating a nicotine resistant microorganism, the method comprising: (a) culturing a microorganism in a medium conducive to growth, wherein the medium comprises a first concentration of nicotine that retards but does not inhibit growth of the microorganism; (b) selecting a single colony of the microorganism and inoculating the single colony into a fresh culture of the medium conducive to growth, wherein the fresh medium comprises a second concentration of nicotine that is incrementally higher than the first concentration and that retards but does not inhibit growth of the microorganism; and (c) repeating step (b) until the desired concentration of nicotine is achieved or until growth of the microorganism is completely inhibited, such that the microorganism produced is resistant to the desired concentration of nicotine.

In one embodiment, the presently disclosed subject matter provides a biologically pure culture of a nicotine resistant *Saccharomyces cerevisiae* strain or a mutant thereof having all the identifying characteristics thereof.

In one embodiment, the presently disclosed subject matter provides a method for producing ethanol from tobacco biomass, the method comprising fermenting a tobacco biomass extract with a nicotine resistant microorganism produced according to a process comprising: (a) culturing a microorganism in a medium conducive to growth, wherein the medium comprises a first concentration of nicotine that retards but does not inhibit growth of the microorganism; (b) selecting a single colony of the microorganism and inoculating the single colony into a fresh culture of the medium conducive to growth, wherein the fresh medium comprises a second concentration of nicotine that is incrementally higher than the first concentration and that retards but does not inhibit growth of the microorganism; and (c) repeating step (b) until the desired concentration of nicotine is achieved or until growth of the microorganism is completely inhibited, wherein ethanol is produced from the fermentation of the tobacco biomass with the nicotine resistant microorganism.

In one embodiment, the presently disclosed subject matter provides a method for producing ethanol from tobacco biomass, the method comprising fermenting a tobacco biomass extract with a biologically pure culture of a nicotine resistant *Saccharomyces cerevisiae* strain or a mutant thereof having all the identifying characteristics thereof, wherein ethanol is produced from the fermentation of the tobacco biomass with the nicotine resistant *Saccharomyces cerevisiae* strain.

BRIEF DESCRIPTION OF THE DRAWINGS

The foregoing aspects and other features of the invention are explained in the following description, taken in connection with the accompanying drawings.

DETAILED DESCRIPTION OF THE INVENTION

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

As used herein, for the purposes of the specification and claims, the term "tobacco biomass" is intended to broadly encompass a whole tobacco plant, any tissue or portion of a tobacco plant, juice of a tobacco plant, and an extracted tobacco biomass.

Figure 1:
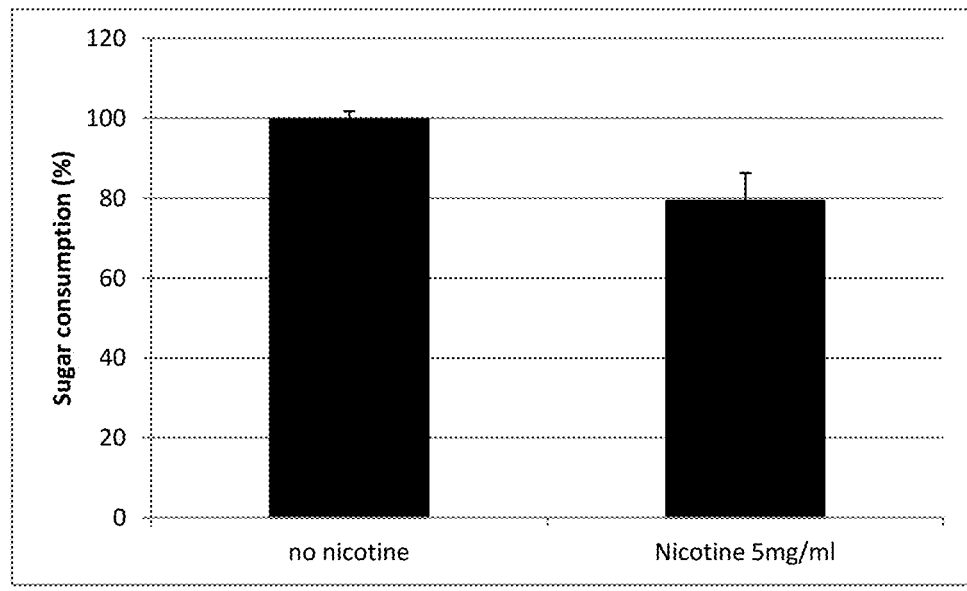
FIG. 1 is a graph showing the inhibitory effect on yeast fermentation (% sugar consumption) when 5 mg/ml nicotine is added to the fermentation solution according to one or more embodiments of the presently disclosed subject matter.
Figure 2:
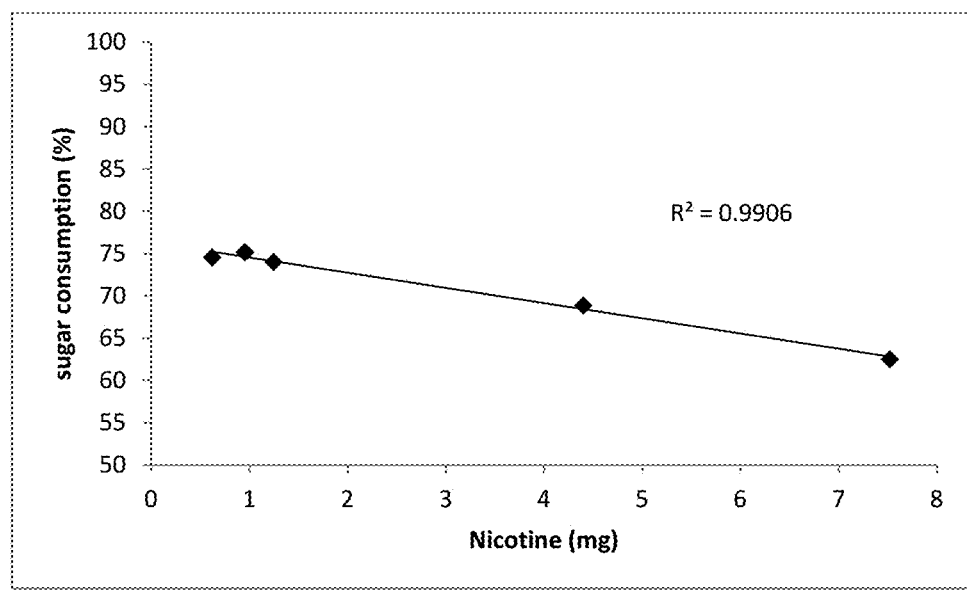
FIG. 2 is a graph showing the inhibitory effect of increased nicotine content on yeast fermentation (sugar consumption %) in fermentation reactions using five different varieties of tobacco as the biomass feedstock, each having different nicotine content (diamond symbols), according to one or more embodiments of the presently disclosed subject matter.

The present inventors have demonstrated that nicotine levels present in traditional tobacco plant biomass inhibits yeast growth, which results in diminished ethanol production in fermentation reactions using tobacco biomass as the feedstock. For example, in FIG. 1, nicotine (5 mg/ml) was added into a fermentation solution and resulted in 21% less sugar consumption by yeast. Thus, in the presence of 0.5% nicotine, 21% less ethanol production can be expected. Traditional tobacco varieties contain about 1% to 2% nicotine in the tobacco biomass, and thus even greater inhibition can be expected. FIG. 2 is a graph showing the inhibitory effect of increased nicotine content on yeast fermentation (sugar consumption %) in fermentation reactions using five different varieties of tobacco as the biomass feedstock, each having different nicotine content (diamond symbols). The graph shows that the sugar consumption rate decreases linearly with increasing nicotine concentration in the tobacco biomass.

As a solution to the problem of nicotine inhibition of fermentation when tobacco biomass is used as the feedstock, the presently disclosed subject matter provides new microbial strains capable of producing high yields of ethanol in the presence of the relatively high nicotine concentrations typical for fermentation of tobacco biomass from commercially grown plants. The methods provided herein for generating the new nicotine resistant strains do not involve genetic engineering. For example, the methods provided herein include: (a) culturing a microorganism in a medium conducive to growth, wherein the medium includes a first concentration of nicotine that retards but does not inhibit growth of the microorganism; (b) selecting a single colony of the microorganism and inoculating the single colony into a fresh culture of the medium conducive to growth, wherein the fresh medium includes a second concentration of nicotine that is incrementally higher than the first concentration and that retards but does not inhibit growth of the microorganism; and (c) repeating step (b) until the desired concentration of nicotine is achieved or until growth of the microorganism is completely inhibited, such that the microorganism produced is resistant to the desired concentration of nicotine.

Figure 3A:
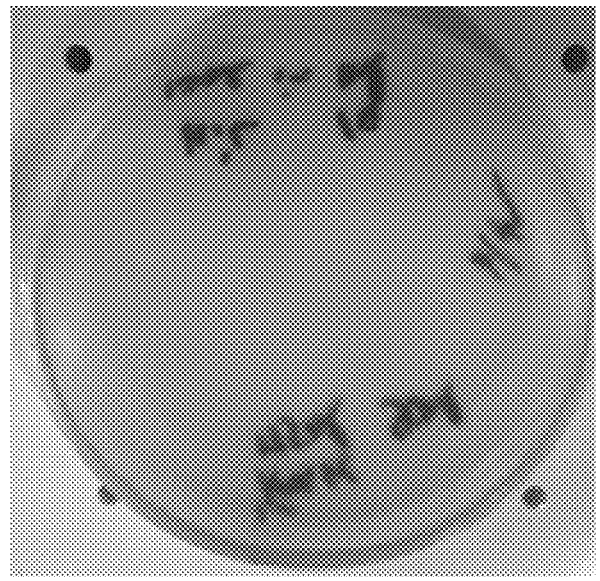
FIGS. 3A-3B are images of culture plates in which A) an X-PRESS yeast strain (LIQUOR QUIK INTERNATIONAL) or B) a nicotine resistant yeast strain generated according to embodiments of the presently disclosed subject matter was inoculated onto a nicotine-containing culture plate (nicotine 50 mg/ml, yeast extract 5 g/L, peptone 10 g/L and agar 15 g/L) and incubated at 27° C. for 3 days.
Figure 3B:

In one aspect, the presently disclosed subject matter provides a nicotine resistant *Saccharomyces cerevisiae* yeast strain generated according to the methods of the present disclosure such that the strain is capable of growing under high nicotine concentration. FIGS. 3A & 3B show how a nicotine resistant yeast strain generated according to the methods of the present disclosure was able to grow on culture containing 50 mg/ml nicotine (FIG. 3A), whereas no growth was observed for the commercially available yeast strain (X-PRESS; LIQUOR QUIK INTERNATIONAL) on this same culture (FIG. 3B).

Figure 4:
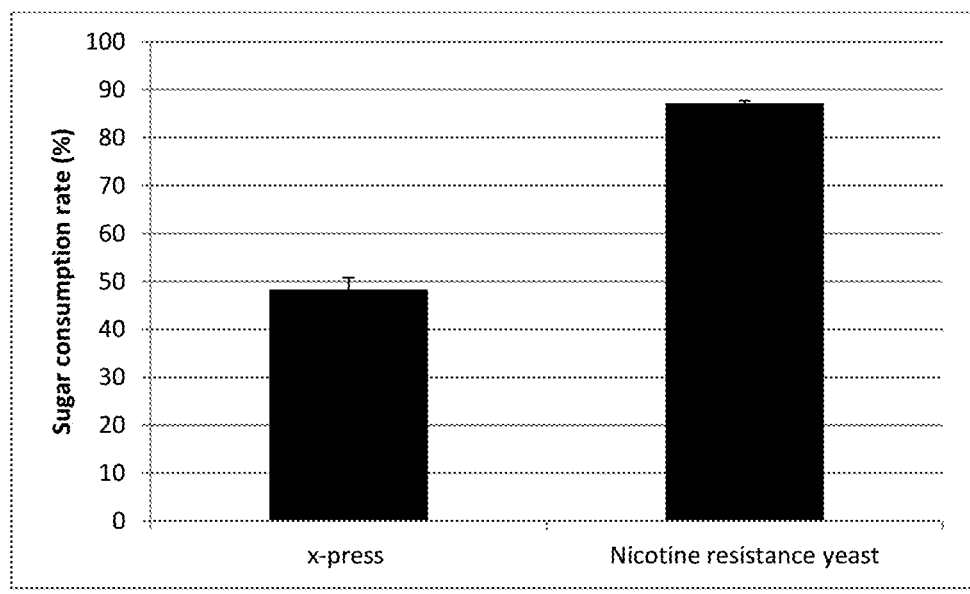
FIG. 4 is a bar graph showing the improved fermentation rate (Sugar consumption rate (%)) for a nicotine resistant yeast generated according to embodiments of the presently disclosed subject matter as compared to an X-PRESS yeast strain when tobacco biomass extract mixed with peptone 10 g/L and yeast extract 5 g/L is the fermentation medium after 72 hr of fermentation at 27° C.

The compositions and methods of the present disclosure expand the utility of ethanol production form tobacco biomass. The new nicotine resistant microorganisms can be capable of growing under high nicotine levels and, thus, can enhance ethanol production from tobacco biomass. For example, a nicotine resistant yeast strain generated according to the methods of the presently disclosed subject matter was tested for its alcohol production during fermentation of tobacco biomass. The results of this experiment are shown in FIG. 4, where the nicotine resistant strain showed a much higher alcohol production during fermentation of tobacco biomass compared to the original X-PRESS strain. In this 72 hr fermentation experiment with tobacco biomass sugar extracts, the original commercially available X-PRESS strain was able to consume only 48.3% of total sugar in comparison to 87.2% of total sugar consumption for the nicotine resistant strain. This is nearly a doubling in sugar utilization by the nicotine resistant strain, which correlates to the new nicotine resistant yeast strain having produced up to 160% more ethanol from the tobacco biomass than the original strain.

Figure 5:
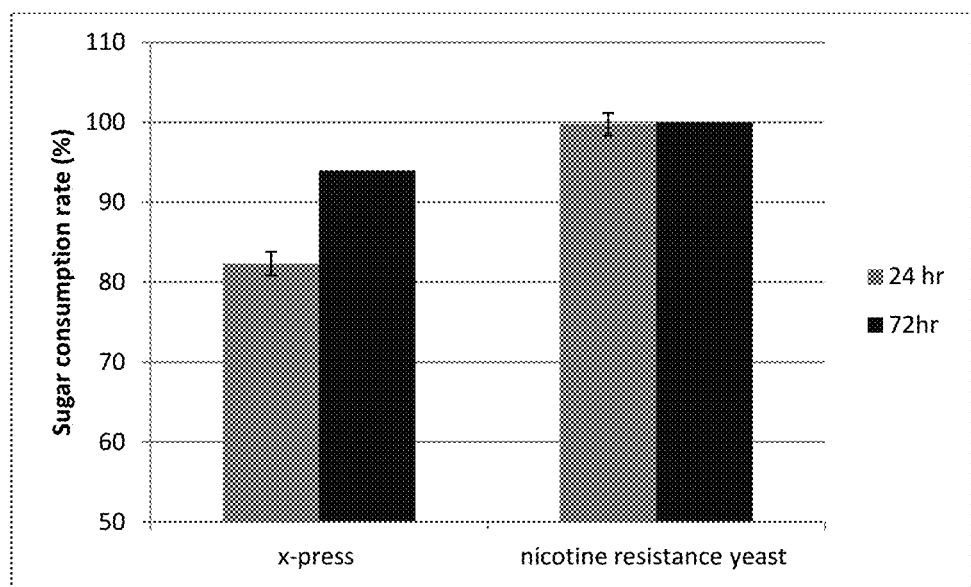
FIG. 5 is a bar graph showing the improvement in sugar consumption (Sugar consumption rate (%)) of tobacco juice fermentation for a nicotine resistant yeast strain generated according to embodiments of the presently disclosed subject matter as compared to an X-PRESS yeast strain (LIQUOR QUIK INTERNATIONAL) with the tobacco juice used as the sugar resource having a nicotine content of 3 mg/ml without addition of extra nutrition such as yeast extract or peptone.

In another example, use of a nicotine resistant *Saccharomyces cerevisiae* strain generated according to the methods of the presently disclosed subject matter for fermentation of tobacco biomass extracts resulted in almost 100% digestion of the free sugar in the tobacco extract, and 100% conversion of the free sugar into ethanol (see FIG. 5). In this experiment tobacco juice was used as fermentation material without addition of extra nutrition such as yeast extract or peptone. The nicotine content of the tobacco juice in this experiment was 3 mg/ml. The original X-PRESS strain utilized 82.3% of total sugar in a 24 hr fermentation process and 94.0% in 72 hr (see FIG. 5). In contrast, the nicotine resistant yeast of the present disclosure consumed almost 100% of the total sugar in 24 hr of the fermentation which was a significant improvement over the X-PRESS yeast. More specifically, under the same conditions, the nicotine resistant strain utilized 99.7% of total sugar in 24 hr of the fermentation and 100% in 72 hr. These results represent a significant improvement in ethanol yield in comparison to fermentation of tobacco biomass using commercially available yeast strain. The amount of ethanol produced from the fermentation of tobacco biomass can be increased by 40% or greater as a result of use of the nicotine resistant *Saccharomyces cerevisiae* strain of the present disclosure.

The results of these two experiments demonstrate that nicotine resistant yeast generated according to the methods of the present disclosure can not only significantly improve ethanol production in tobacco biomass extract fermentations, but can also shorten the fermentation time.

In one embodiment, the presently disclosed subject matter provides a nicotine resistant microorganism produced according to a process comprising: (a) culturing a microorganism in a medium conducive to growth, wherein the medium comprises a first concentration of nicotine that retards but does not inhibit growth of the microorganism; (b) selecting a single colony of the microorganism and inoculating the single colony into a fresh culture of the medium conducive to growth, wherein the fresh medium comprises a second concentration of nicotine that is incrementally higher than the first concentration and that retards but does not inhibit growth of the microorganism; and (c) repeating step (b) until the desired concentration of nicotine is achieved or until growth of the microorganism is completely inhibited, wherein the microorganism produced is resistant to the desired concentration of nicotine.

The nicotine resistant microorganism can be a yeast. The nicotine resistant yeast can be a *Saccharomyces cerevisiae*.

In the process for producing the nicotine resistant microorganism, the first concentration of nicotine can range from about 0.5% w/v to about 1.5% w/v nicotine. In the process, the incrementally higher concentration of nicotine can be an incremental increase of about 0.5% w/v. In the process, the microorganism can be cultured in the medium conducive to growth for a length of time sufficient for the microorganism to reach a growth plateau.

In one embodiment, the presently disclosed subject matter provides a method for generating a nicotine resistant microorganism, the method comprising: (a) culturing a microorganism in a medium conducive to growth, wherein the medium comprises a first concentration of nicotine that retards but does not inhibit growth of the microorganism; (b) selecting a single colony of the microorganism and inoculating the single colony into a fresh culture of the medium conducive to growth, wherein the fresh medium comprises a second concentration of nicotine that is incrementally higher than the first concentration and that retards but does not inhibit growth of the microorganism; and (c) repeating step (b) until the desired concentration of nicotine is achieved or until growth of the microorganism is completely inhibited, wherein the microorganism produced is resistant to the desired concentration of nicotine.

In the method for generating a nicotine resistant microorganism, the microorganism can be a yeast. The yeast can be a *Saccharomyces cerevisiae*.

In the method for generating the nicotine resistant microorganism, the first concentration of nicotine can range from about 0.5% w/v to about 1.5% w/v nicotine. In the method, the incrementally higher concentration of nicotine can be an incremental increase of about 0.5% w/v. In the method, the microorganism can be cultured in the medium conducive to growth for a length of time sufficient for the microorganism to reach a growth plateau.

In one embodiment, the presently disclosed subject matter provides a biologically pure culture of a nicotine resistant *Saccharomyces cerevisiae* strain, or a mutant thereof having all the identifying characteristics thereof.

In one embodiment, the presently disclosed subject matter provides a method for producing ethanol from tobacco biomass, the method comprising fermenting a tobacco biomass extract with a nicotine resistant microorganism produced according to a process comprising: (a) culturing a microorganism in a medium conducive to growth, wherein the medium comprises a first concentration of nicotine that retards but does not inhibit growth of the microorganism; (b) selecting a single colony of the microorganism and inoculating the single colony into a fresh culture of the medium conducive to growth, wherein the fresh medium comprises a second concentration of nicotine that is incrementally higher than the first concentration and that retards but does not inhibit growth of the microorganism; and (c) repeating step (b) until the desired concentration of nicotine is achieved or until growth of the microorganism is completely inhibited, wherein ethanol is produced from the fermentation of the tobacco biomass extract with the nicotine resistant microorganism.

In the method for producing ethanol from tobacco biomass, the amount of ethanol produced from the fermentation can be increased by 30% or greater due to use of the nicotine resistant microorganism. The amount of ethanol produced from the fermentation can be increased by greater than about 40%, 50%, 60%, 70%, 80%, 90%, 100%, or 150% or even greater.

In one embodiment, the presently disclosed subject matter provides a method for producing ethanol from tobacco biomass, the method comprising fermenting a tobacco biomass extract with a biologically pure culture of a nicotine resistant *Saccharomyces cerevisiae* strain, or a mutant thereof having all the identifying characteristics thereof, wherein ethanol is produced from the fermentation.

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

EXAMPLES

Example 1

Generation of a Nicotine Resistant Yeast Strain

A yeast strain having resistance to nicotine was generated to solve the problem of the reduced production of ethanol from fermentation of tobacco biomass feedstock relative to other cellulosic feedstocks.

To begin, several commercially available yeast strains were tested in tobacco biomass fermentation reactions. One of the strains tested was a *Saccharomyces cerevisiae* called X-PRESS (X-PRESS SUPER YEAST X-PRESS 20% ABV; LIQUOR QUIK INTERNATIONAL) and this strain was determined to be the best of the strains tested in terms of efficacy of ethanol production. However, while this strain showed the best alcohol production, it was determined that the nicotine naturally present in the tobacco biomass was inhibiting the growth of the yeast during the fermentation process, which negatively affected the amount of ethanol that could be produced in the fermentation (see FIG. 1 and FIG. 2). In FIG. 1, nicotine (5 mg/ml) was added into a fermentation solution and resulted in 21% less sugar consumption by yeast. Thus, in the presence of 0.5% nicotine, 21% less ethanol production can be expected. Traditional tobacco varieties contain about 1% to 2% nicotine in the tobacco biomass, and thus even greater inhibition can be expected. FIG. 2 is a graph showing the inhibitory effect of increased nicotine content on yeast fermentation (sugar consumption %) in fermentation reactions using five different varieties of tobacco as the biomass feedstock, each having different nicotine content (diamond symbols). The graph shows that the sugar consumption rate decreases linearly with increasing nicotine concentration in the tobacco biomass.

Thus, in order to work around the problem of nicotine inhibition, a method was designed to generate a new yeast strain capable of retaining high ethanol production even in the presence of the nicotine concentrations typically found in tobacco biomass. The commercially available yeast strain X-PRESS described above was chosen for these experiments. The commercial X-PRESS strain was able to utilize about 50% of the sugars in the tobacco biomass for fermentation.

The following method was developed to generate a new yeast strain that would possess high fermentation efficiency even in the presence of high nicotine concentration. In the method, the X-PRESS yeast strain was subjected to a number of selection cycles to generate nicotine resistance. First, the X-PRESS yeast strain was cultured in liquid media (YP medium containing yeast extract (5 g/L); peptone (10 g/L)) to which 1% w/v (10 mg/ml) nicotine was added for 72 hr at 27° C. with shaking 200 rpm. This nicotine concentration inhibited the growth rate, but did not kill the yeast. After 72 hr, 100 µl of the culture was applied to a 1% w/v nicotine YP agar plate and allowed to grow on the plate at 27° C. for another 72 hr. In the next step, a single colony was inoculated into a 1.5% w/v nicotine YP medium solution and incubated for another 72 hr and the entire process was repeated. This process was repeated multiple times with the concentration of nicotine being increased in increments of 0.5% w/v at each cycle. At a nicotine concentration of 7.5%, no surviving yeast colonies of the original X-PRESS yeast strain were observable while the newly developed yeast nicotine resistant yeast was still able to grow (see FIG. 3A and FIG. 3B). In FIGS. 3A & 3B, the yeast strains were inoculated onto a nicotine-containing culture plate (nicotine 50 mg/ml, yeast extract 5 g/L, peptone 10 g/L and agar 15 g/L) and incubated at 27° C. for 3 days. No yeast growth could be observed on the plate in FIG. 3A which indicates X-PRESS yeast was killed by this nicotine concentration, while the nicotine resistant yeast grew well under these conditions (FIG. 3B).

Thus, a new yeast strain was created having high resistance to nicotine. To ensure the stability of the nicotine resistance trait, an additional 20 generations of the resistant strain were cultured in the 7.5% w/v nicotine nutrient solution. In addition, further experiments demonstrated that this nicotine resistant strain is capable of growing in medium containing 10% w/v and higher nicotine concentrations (data not shown). The nicotine resistant yeast grew well under these conditions.

The newly generated nicotine resistant strain was tested for its alcohol production during fermentation of tobacco biomass. In this first experiment, the nicotine resistant strain showed a much higher alcohol production during fermentation of tobacco biomass compared to the original X-PRESS strain. Specifically, tobacco biomass extract was mixed with peptone 10 g/L and yeast extract 5 g/L for the fermentation. The X-PRESS and nicotine resistant yeast strains were added into the solution and incubated at 27° C. for 72 hr. In this 72 hr fermentation experiment with tobacco biomass sugar extracts, the original X-PRESS strain was able to consume only 48.3% of total sugar in comparison to 87.2% of total sugar consumption for the nicotine resistant strain (see FIG. 4). This is nearly a doubling in sugar utilization by the nicotine resistant strain, which correlates to the new yeast strain having produced up to 160% more ethanol from the tobacco biomass than the original strain.

In a second experiment in which tobacco juice was used as fermentation material without addition of extra nutrition such as yeast extract or peptone, the original X-PRESS strain utilized 82.3% of total sugar in a 24 hr fermentation process and 94.0% in 72 hr (see FIG. 5). The nicotine content of the tobacco juice in this experiment was 3 mg/ml. The results in FIG. 5 show that the nicotine resistant yeast consumed almost 100% of the total sugar in 24 hr of the fermentation which was a significant improvement over the X-PRESS yeast. More specifically, under the same conditions, the nicotine resistant strain utilized 99.7% of total sugar in 24 hr of the fermentation and 100% in 72 hr.

The results of these two experiments demonstrate that the new nicotine resistant yeast strain not only significantly improved ethanol production in tobacco biomass extract fermentations, but also shortened the fermentation time for fermentations based on tobacco juice as the sugar resource.

Any patents or publications mentioned in this specification are indicative of the levels of those skilled in the art to which the present disclosure pertains. These patents and publications are herein incorporated by reference in their entirety to the same extent as if each individual publication was specifically and individually indicated to be incorporated by reference.

One skilled in the art will readily appreciate that the present disclosure is well adapted to carry out the objects and obtain the ends and advantages mentioned, as well as those inherent therein. The present Examples along with the methods described herein are presently representative of preferred embodiments, are exemplary, and are not intended as limitations on the scope of the invention. Changes therein and other uses will occur to those skilled in the art which are encompassed within the spirit of the present disclosure as defined by the scope of the claims.

That which is claimed:

1. A method for generating a nicotine resistant microorganism, the method comprising:
   (a) culturing a microorganism in a medium conducive to growth, wherein the medium comprises a first concentration of nicotine that retards but does not inhibit growth of the microorganism;
   (b) selecting a single colony of the microorganism and inoculating the single colony into a fresh culture of the medium conducive to growth, wherein the fresh medium comprises a second concentration of nicotine that is incrementally higher than the first concentration and that retards but does not inhibit growth of the microorganism; and (c) repeating step (b) until the desired concentration of nicotine is achieved or until growth of the microorganism is completely inhibited, wherein the microorganism produced is resistant to the desired concentration of nicotine.

2. The method of claim 1, wherein the microorganism is a yeast.

3. The method of claim 2, wherein the yeast is a *Saccharomyces cerevisiae*.

4. The method of claim 1, wherein the first concentration of nicotine ranges from about 0.5% w/v to about 1.5% w/v nicotine.

5. The method of claim 1, wherein the incrementally higher concentration of nicotine is an incremental increase of about 0.5% w/v.

6. The method of claim 1, wherein the microorganism is cultured in the medium conducive to growth for a length of time sufficient for the microorganism to reach a growth plateau.

7. A method for producing ethanol from tobacco biomass, the method comprising:
 (i) fermenting a tobacco biomass extract with a nicotine resistant microorganism, wherein ethanol is produced from the fermentation and wherein the nicotine resistant microorganism is produced according to a process comprising:
  (a) culturing a microorganism in a medium conducive to growth, wherein the medium comprises a first concentration of nicotine that retards but does not inhibit growth of the microorganism;
  (b) selecting a single colony of the microorganism and inoculating the single colony into a fresh culture of the medium conducive to growth, wherein the fresh medium comprises a second concentration of nicotine that is incrementally higher than the first concentration and that retards but does not inhibit growth of the microorganism; and
  (c) repeating step (b) until the desired concentration of nicotine is achieved or until growth of the microorganism is completely inhibited, wherein the microorganism produced is resistant to the desired concentration of nicotine; and
 (ii) isolating the ethanol produced in step (i).

8. The method of claim 7, wherein the amount of ethanol produced from the fermentation is increased by 40% or greater due to use of the nicotine resistant microorganism.

9. The method of claim 7, wherein the amount of ethanol produced from the fermentation is increased by 80% or greater due to use of the nicotine resistant microorganism.

10. The method of claim 7, wherein the nicotine resistant microorganism is a yeast.

11. The method of claim 10, wherein the yeast is a *Saccharomyces cerevisiae*.

12. The method of claim 7, wherein the first concentration of nicotine ranges from about 0.5% w/v to about 1.5% w/v nicotine.

13. The method of claim 7, wherein the incrementally higher concentration of nicotine is an incremental increase of about 0.5% w/v.

14. The method of claim 7, wherein the microorganism is cultured in the medium conducive to growth for a length of time sufficient for the microorganism to reach a growth plateau.

* * * * *